United States Patent [19]
Yazawa et al.

[11] Patent Number: 5,628,763
[45] Date of Patent: May 13, 1997

[54] SURGICAL HANDPIECE

[75] Inventors: Chikao Yazawa; Takasuke Nakanishi, both of Kanuma, Japan

[73] Assignee: Nakanishi, Inc., Tochigi-ken, Japan

[21] Appl. No.: 653,543

[22] Filed: May 24, 1996

[30] Foreign Application Priority Data

May 25, 1995 [JP] Japan ................... 7-126332

[51] Int. Cl.$^6$ ............................... A61B 17/32
[52] U.S. Cl. ........................... 606/170; 606/180
[58] Field of Search .................... 606/167, 169, 606/170–171, 180, 79–80, 84

[56] References Cited

U.S. PATENT DOCUMENTS

| | | | |
|---|---|---|---|
| 3,308,828 | 3/1967 | Pippin | 606/180 |
| 3,835,858 | 9/1974 | Hagen | 606/180 |
| 4,070,030 | 1/1978 | Hedrick | 606/180 X |
| 4,436,091 | 3/1984 | Banko | 606/180 X |
| 4,445,509 | 5/1984 | Auth | 606/180 X |
| 4,461,305 | 7/1984 | Cibley | 606/180 X |
| 4,466,429 | 8/1984 | Loscher et al. | 606/180 |
| 5,346,504 | 9/1994 | Ortiz et al. | 606/192 |
| 5,376,097 | 12/1994 | Phillips | 606/151 |
| 5,490,860 | 2/1996 | Middle et al. | 606/171 |
| 5,512,044 | 4/1996 | Duer | 606/180 X |

*Primary Examiner*—Michael Powell Buiz
*Assistant Examiner*—Nancy Connolly Mulcare
*Attorney, Agent, or Firm*—Malcolm B. Wittenberg

[57] ABSTRACT

A surgical handpiece contains a spindle detachably holding an elongate bar for surgical operation and transmitting rotation to the bar, an elongate sheath covering the bar except for the distal portion thereof, and a plurality of balls provided in the proximity of the distal end of the sheath, with the balls being arranged in one cross-sectional plane. The balls have a diameter approximately equal to a thickness of the sheath in the proximity of the distal end thereof, and the balls are projected slightly radially inwardly from the inner surface of the sheath with the peripheral surface of the ball being spaced from the bar.

5 Claims, 4 Drawing Sheets

SURGICAL HANDPIECE

BACKGROUND OF THE INVENTION

This invention relates to a surgical handpiece for use in a surgical operation.

A surgical handpiece has an elongate distal portion tapered toward the tip thereof so that the handpiece can easily be inserted into an extremely narrow diseased part such as inside the ears. The smaller the diameter of the distal portion of the handpiece, the more practical the handpiece is. However, there is a limitation on reducing the diameter of a casing portion containing a spindle therein which hold and rotationaly drive a bar of a drill and the like used for treatment of the diseased part. Therefore, the surgical handpiece is so designed that the longitudinal size of the casing portion is short, while the bar and the sheath covering the bar except for the distal end portion thereof are elongate.

The revolution speed of the bar during the operation is in the high revolution speed zone (revolution speed of 70,000 to 100,000 rpm), wherein the bar is able to cut even a bone.

The handpiece is also provided with ball bearings and the like disposed in the intermediate portion of the length of the sheath for preventing the friction of the bar. If the ball bearings and the like are positioned in the proximity of the sheath tip, the diameter of the sheath becomes too large to reach a narrow diseased part.

However, with the conventional surgical handpiece, the bar is likely to deflect when the bar receives a large load, thereby contacting with the inner surface of the sheath tip to cause abrasion and heating. In order to eliminate the contact between the bar and the inner surface of the sheath as much as possible, the bar is relatively well spaced from the inner surface of the sheath. But this space affects adversely to put a limit on reducing the diameter of the distal portion of the sheath, i.e. the distal portion of the handpiece.

SUMMARY OF THE INVENTION

It is therefore an object of the present invention to provide a surgical handpiece wherein the contact between and thus the abrasion of the bar and the inner surface of the sheath are prevented, and the heating occurred between the sheath tip and the bar is minimized.

It is another object of the present invention to provide a surgical handpiece wherein the diameter of the distal portion thereof can be designed still smaller than that of the conventional surgical handpiece.

These and other objects of the present invention will become apparent from the following description with reference to the attached drawings.

According to the present invention, there is provided a surgical handpiece comprising a spindle detachably holding an elongate bar for surgical operation and transmitting rotation to said bar, an elongate sheath covering said bar except for a distal end portion thereof, and a plurality of balls provided in a proximity of a distal end of said sheath, said balls being arranged in one cross-sectional plane, wherein said balls have a diameter approximately equal to a thickness of said sheath in the proximity of the distal end thereof, and said balls are projected slightly radially inwardly from an inner surface of said sheath with a peripheral surface of said ball being spaced from the bar.

PREFERRED EMBODIMENTS OF THE INVENTION

The present invention is explained with reference to the attached drawings.

Figure 1:
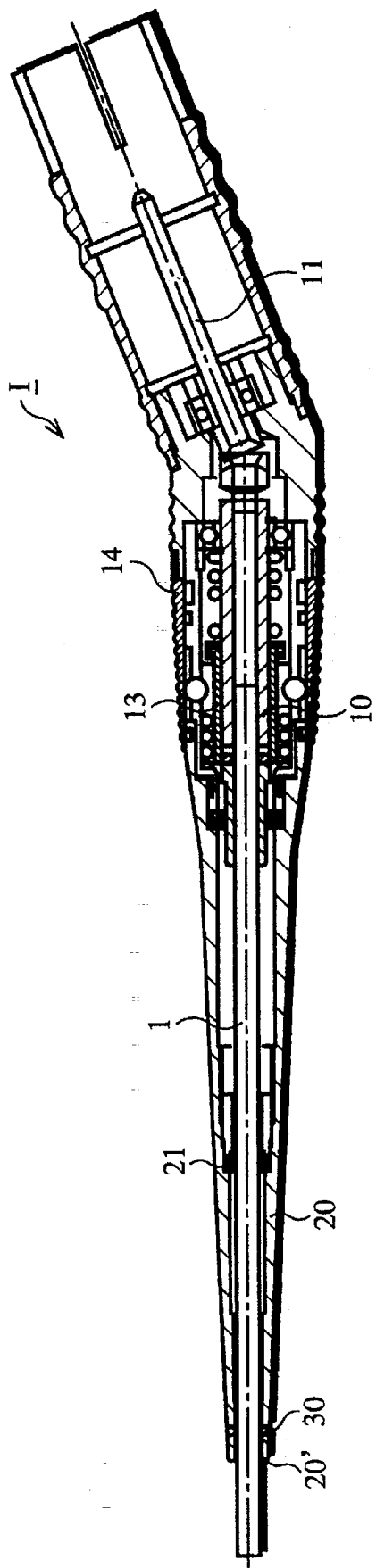
FIG. 1 is a cross-sectional view depicting a surgical handpiece of the present invention.

FIG. 1 is a cross-sectional view showing a surgical handpiece I of the present invention. The handpiece I has a spindle 10 detachably holding the proximal end portion of an elongate bar 1 for surgical operation to transmit high speed revolution (70,000 to 100,000 rpm.) to the bar 1, and an approximately cylindrical sheath 20 into which the bar 1 is inserted for covering the bar 1 except for its distal end portion. The bar 1 can be replaced with other bar, and has a tool such as a drill. (not shown) at the tip portion thereof for performing a desired treatment.

Figure 2:
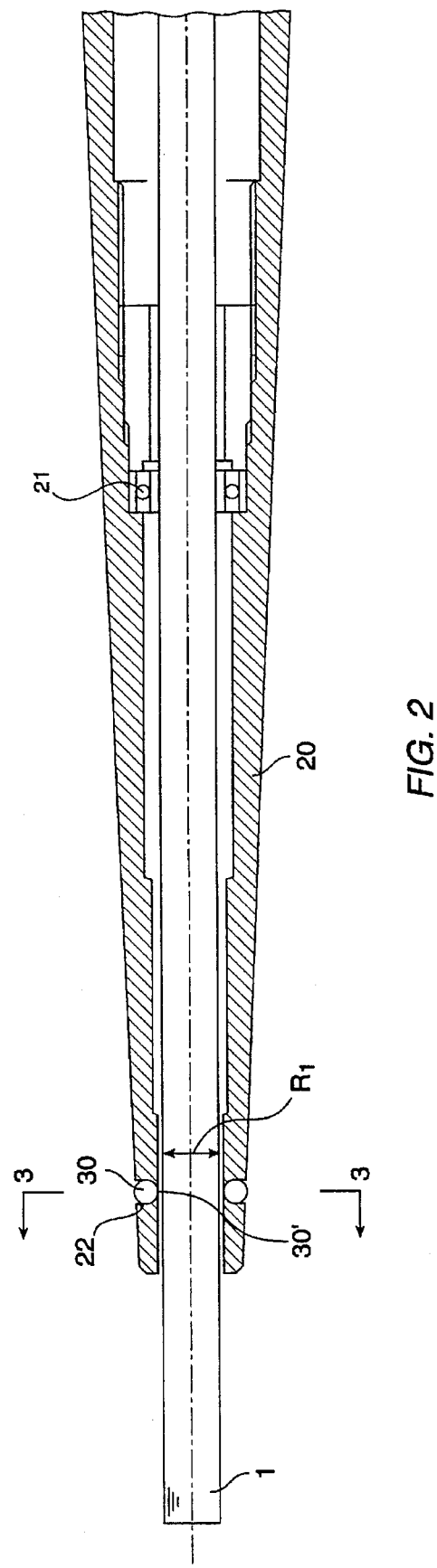
FIG. 2 is an enlarged cross-sectional view depicting a sheath.
Figure 3:
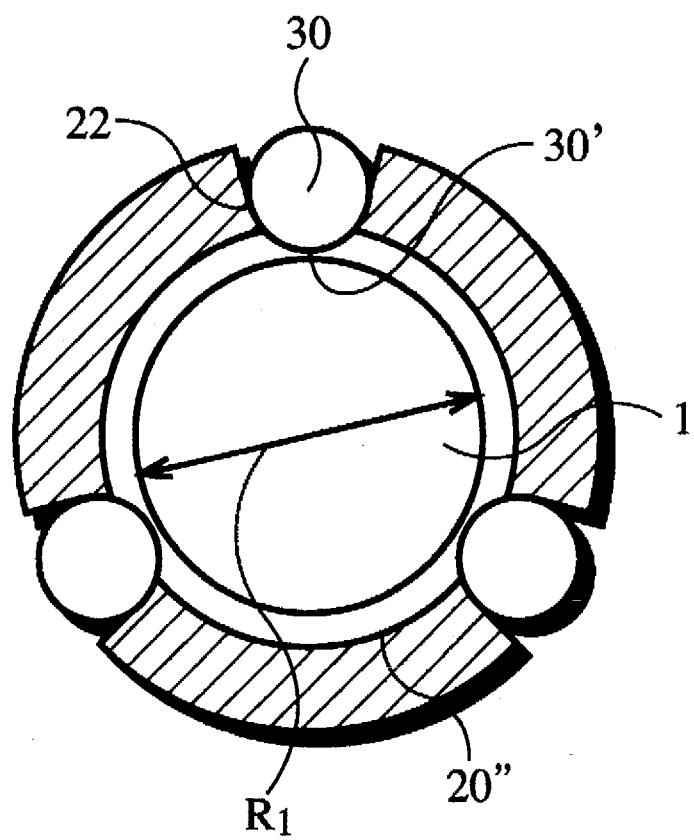
FIG. 3 is a cross-sectional view taken along the line A—A in FIG. 2.

The spindle 10 is rotationally driven by a separate drive unit (not shown) by way of rotary shaft 11 and gears. The casing portion 14 containing the spindle 10 may also contain, for example, a member 13 for preventing the slip-off of the bar 1 during the treatment. Thus, the diameter of the casing portion 14 cannot be reduced extremely, Accordingly, the axial length of the casing portion 14 is formed as short as possible, while the sheath 20 provided distally of the the casing portion 14 is made elongate with the outer diameter gradually reduced toward the tip 20', thereby forming a practical handpiece I having a tapered distal portion, Ball bearings 21 are provided in the intermediate portion of the length of the sheath 20 for preventing the friction of the bar 1, These bearings 21 cannot be positioned in the proximity of the tip of the sheath 20 since this positioning is not practical, FIG. 2 is an enlarged cross-sectional view of the sheath 20, and FIG. 3 is a cross-sectional view taken along the line A—A in FIG. 2.

In the proximity of the distal end of the sheath 20, three balls 30 are arranged in one cross-sectional plane perpendicular to the longitudinal axis of the sheath 20 and displaced at an equal angular distance (120°) from each other along a circumference of the sheath 20. Each ball 30 is fixed within an aperture 22 penetrating the sheath 20 by means of press fitting, adhesion, or the like method. The diameter of the ball 30 is approximately equal to, but may be slightly larger than the thickness of the sheath 20 around the aperture 22. The ball 30 is positioned so that the peripheral surface 30' of the ball 30 is slightly projected radially inwardly from the inner surface 20" of the sheath 20, but is placed slightly radially outwardly of the outer peripheral surface of the bar 1 (outer diameter $R_1$). Accordingly, the bar 1 is spaced from the peripheral surface 30' of the ball 30 and contacts neither of the balls 30 in the normal state. But when the bar 1 is deflected due to the load applied during the operation, the bar 1 is brought into contact with the peripheral surface 30' of the ball 30. Consequently, the deflection of the bar 1 is restrained by the balls 30, and the bar 1 is prevented from contacting the inner surface 20" of the sheath 20. Here, since the bar 1 point-contacts with the ball 30, the bar 1 is not abraded through the contact with the ball 30, and the heat generated by the contact between the bar 1 and the ball 30 is minimized to the allowable range.

Figure 4:
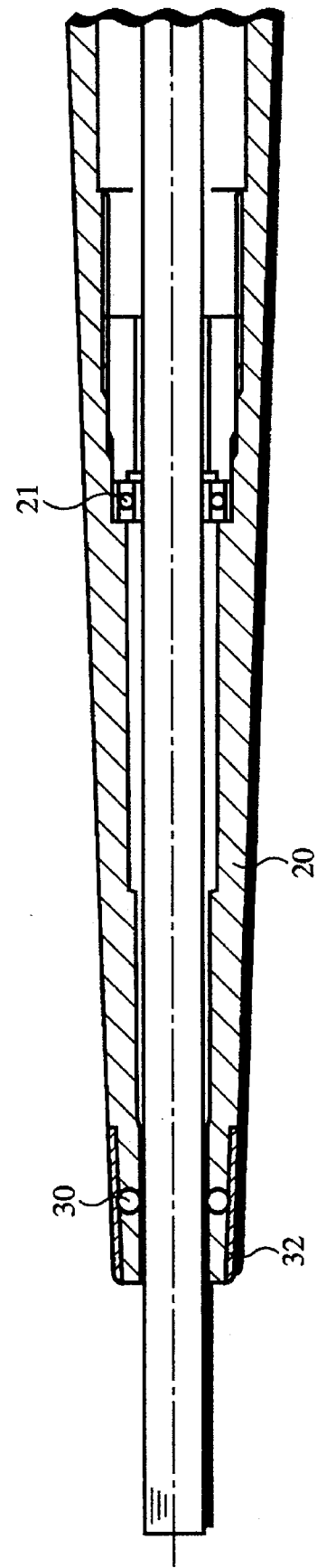
FIG. 4 is a cross-sectional view depicting another embodiment of the present invention with a ball cover disposed in the proximity of a sheath tip.

FIG. 4 shows another embodiment, wherein a ball cover 32 is provided in the proximity of the distal end of the sheath 20. The ball cover 32 securely prevents, the balls 30 from dropping off the aperture 22.

As described above, according to the present invention, the deflection of the bar due to the load applied during the operation is restrained by the plurality of balls fixed in the proximity of the sheath tip, thereby preventing the bar from contacting the inner surface of the sheath. Therefore, the abrasion of the inner surface of the sheath is avoided.

Although the present invention has been described with reference to the preferred embodiment, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A surgical handpiece comprising a spindle detachably holding an elongate bar for surgical operation and transmitting rotation to said bar, an elongate sheath covering said bar except for a distal end portion thereof, and a plurality of balls provided in a proximity of a distal end of said sheath, said balls being arranged in one cross-sectional plane, wherein said balls have a diameter approximately equal to a thickness of said sheath in the proximity of the distal end thereof, and said balls are projected slightly radially inwardly from an inner surface of said sheath with a peripheral surface of said ball being spaced from the bar.

2. The surgical handpiece as claimed in claim 1 further comprising a ball bearing disposed in an intermediate portion of a length of said sheath for preventing friction of the bar.

3. The surgical handpiece as claimed in claim 1 further comprising a member for preventing said bar from slipping off the spindle.

4. The surgical handpiece as claimed in claim 1 wherein said handpiece has three of said balls arranged in one cross-sectional plane at an angular distance of 120° from each other along a circumference of said sheath.

5. The surgical handpiece as claimed in claim 1 further comprising a bail cover for preventing said balls from dropping off said sheath.

* * * * *